United States Patent [19]

Paulsen et al.

[11] 4,195,173
[45] Mar. 25, 1980

[54] PROCESS FOR PREPARING PSEUDO-DISACCHARIDES

[75] Inventors: Hans Paulsen; Rolf Jansen, both of Hamburg; Peter Stadler, Haan, all of Fed. Rep. of Germany

[73] Assignee: Bayer Aktiengesellschaft, Leverkusen, Fed. Rep. of Germany

[21] Appl. No.: 915,473

[22] Filed: Jun. 14, 1978

[30] Foreign Application Priority Data

Jul. 5, 1977 [DE] Fed. Rep. of Germany ....... 2730372

[51] Int. Cl.$^2$ ........................................... C07H 15/22
[52] U.S. Cl. .................................. 536/17 R; 536/10; 424/180
[58] Field of Search ................................... 536/17, 10

[56] References Cited

U.S. PATENT DOCUMENTS

| | | | |
|---|---|---|---|
| 4,031,210 | 6/1977 | Chazen et al. | 536/17 |
| 4,044,123 | 8/1977 | Daniels et al. | 536/17 |
| 4,063,015 | 12/1977 | Mallams | 536/17 |
| 4,093,797 | 6/1978 | Oda et al. | 536/17 |

*Primary Examiner*—Johnnie R. Brown
*Attorney, Agent, or Firm*—Sprung, Felfe, Horn, Lynch & Kramer

[57] ABSTRACT

The invention provides pseudo-disaccharides (and their salts) and a method for their preparation. The pseudo-disaccharides are useful as intermediates for the preparation of antibiotics and are also useful as antimicrobial agents, particularly against Gram-negative bacteria.

3 Claims, No Drawings

PROCESS FOR PREPARING PSEUDO-DISACCHARIDES

The invention relates to new pseudo-disaccharides, useful as intermediates for the synthesis of pseudo-trisaccharides and processes for their production.

The present invention provides compounds which are pseudo-disaccharides of the following general formula (I) or their salts

X—O—Y  (I)

in which

Y is a radical of the formula

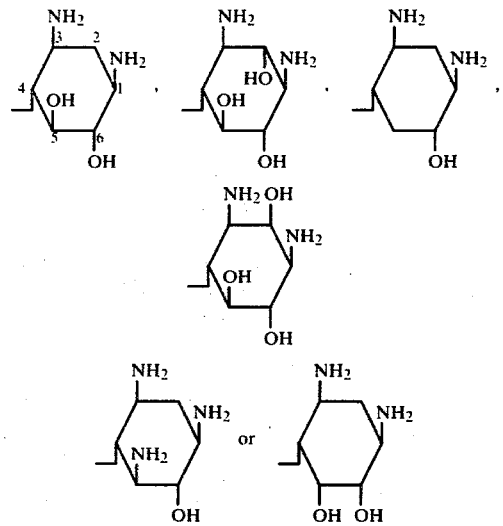

and X is a radical of the formula

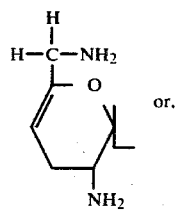

when Y is a radical of the formula

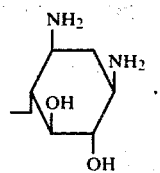

X is a radical of the formula

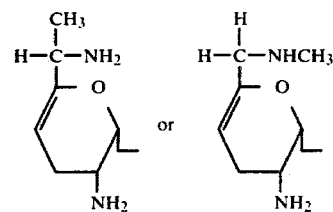

the bond between X and Y being a (1→4)-glycosidic bond in each case.

The compound of the formula (II)

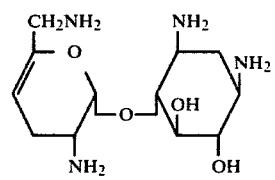

is a particularly valuable pseudo-disaccharide.

The pseudo-disaccharides can be in the free form or in the form of their addition salts with acids, particularly pharmaceutically acceptable acids, such as, for example, hydrochloric, sulphuric, phosphoric, nitric, hydrobromic, benzenesulphonic, formic, acetic, propionic, maleic, ascrobic or citric acid.

The invention furthermore relates to a process for the preparation of compounds of the following general formula (I) or their salts

X—O—Y  (I)

in which

X and Y have the same meaning as defined hereinbefore in which process a compound of the formula (III)

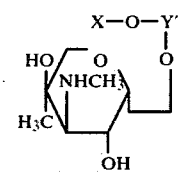

in which

X has the same meaning as defined hereinbefore in formula (I) and

Y' is a radical of the formula

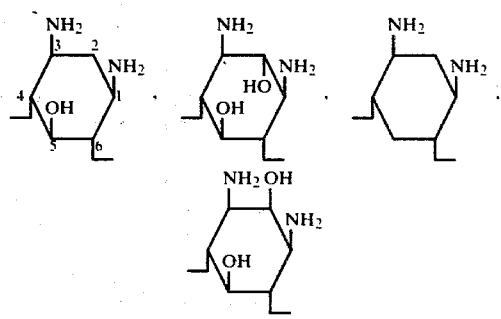

-continued

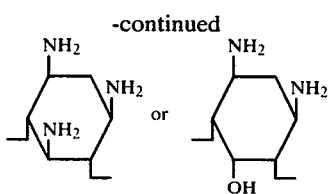

which is linked glycosidically with the radical X in the 4-position and glycosidically with the garosaminyl radical attached to said radical Y' in the 6-position and in which X is a radical of the formula

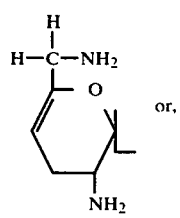

when Y' is a radical of the formula

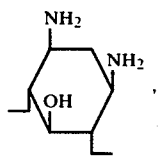

X is a radical of the formula

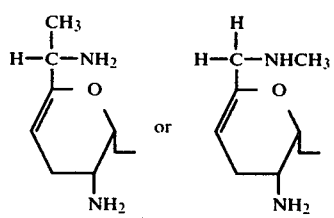

optionally in the form of an N-protected derivative thereof, is cleaved by treatment with an oxidizing agent so as to produce a compound of the formula (I), any protective group which may be present is removed, and the resulting compound of the formula (I) isolated in its free form or, if an acid is present, in the form of an acid addition salt thereof, and if desired said free form or salt is converted into a salt or the free form, respectively.

The starting compounds of the formula (III) are pseudo-trisaccharides which are known from the literature, such as the antibiotics verdamycin, sisomycin, G 52, mutamycin 1, mutamycin 2, mutamycin 4, mutamycin 5 and mutamycin 6 (see DT-OS (German Published Specification) No. 2,436,160).

In some cases it may be advantageous to use selectively N-blocked derivatives of compounds of the formula (III) as starting materials in the preparation of the pseudo-disaccharides according to the invention.

The nature of the blocking should be such that all the amino or methylamino groups present in the molecule, with the exception of the methylamino group present in the garosaminyl radical to be split off, are blocked.

Compounds protected in such a manner are accordingly derivatives of the aminotrisaccharides according to formula (III) which are blocked on the four N atoms 1, 2', 3 and 6' or, in the case of mutamycin 5, on the five N atoms 1, 2', 3, 5 and 6'.

All the protective groups which are stable under the oxidation conditions of the process described above and are customary in the field of amino-sugar and peptide chemistry, can be used as the amino-protective groups. Such protective groups and the processes for their preparation are known (see, for example, Houben-Weyl, Methoden der organischen Chemie (Methods of Organic Chemistry), volume XV, 1, pages 46–305, Georg Thieme Verlag, Stuttgart, 1974).

Those N-protected derivatives of the aminotrisaccharides according to formula (III) which contain acyl protective groups of the type

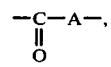

wherein A is a group of the formula (1)

or formula (2)

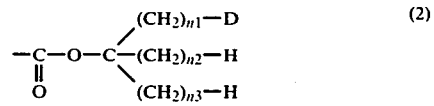

wherein, in the protective group radicals mentioned,

B and D independently of one another are each hydrogen, phenyl or substituted phenyl and $n$, $n_1$, $n_2$ and $n_3$ independently of one another represent a number from 0 to 5, are preferably used for protecting the compounds of formula (III) in the oxidation reaction.

According to a new process (German Patent Application No. P2726197.8-corresponding to our co-pending European Patent Application No. 78100099.7), in order to prepare these selectively protected aminotrisaccharides, an aminotrisaccharide of formula (III) is reacted with a compound of the formula (IV)

in which

A is a radical of formula (1) or (2) as defined hereinbefore and

G' designates halogen or a leaving group customary in acylation reactions, preferably an activating ester, such as phenylester or p-nitrophenylester or a group —O—CO—A, in which A has the same meaning as defined hereinbefore, in an inert solvent, such as DMT, pyridine, acetone, ethanol, optionally with the addition of water desirably at a temperature of from −80° C. to +50° C. in the presence of a base, and the reaction product is worked up in the customary manner.

The customary oxidizing agents can be used to cleave the compounds of formula (III) or their N-blocked derivatives.

Examples of suitable oxidizing agents are heavy metal salts, peroxides, halogens, hydrogen halide acids and their salts, nitrogen oxides and molecular oxygen. Preferred oxidizing agents are permanganates of alkali- and earth-alkali metals, manganates, manganese dioxide, chromium trioxide, alkalimetal, bichromates, chromates, alkyl chromates, chromyl chloride, selenium dioxide, cobalt-III salts, cerium-IV salts, potassium hexacyanoferrate-III, copper oxide, lead oxide, mercury oxide, mixtures of hydrogen peroxide with iron-II salts, iron-III salts, osmium tetroxide, vanadates, tungstic acid and/or chromic acid, lead tetraacetate, chlorine, bromine, iodine, hypochlorites, chlorates, hypobromites, bromates, periodates, dinitrogen monoxide, nitrogen dioxide and air. If molecular oxygen is used, noble metals, such as platinum, palladium, rhodium, ruthenium or rhenium, as well as nickel, are preferably employed as catalysts.

Particularly preferred oxidizing agents are manganese dioxide, sodium periodate, potassium hexacyanoferrate-III and potassium permanganate.

The cleaving reaction is preferably carried out in the presence of a diluent which is inert under the reaction conditions used, preferably one in which the reactants dissolve. Suitable diluents of the type mentioned are methanol, ethanol, i-propanol, tetrahydrofurane, dimethylformamide, dioxane, pyridine and ethylene glycol dimethyl ether, acetone and acetic acid, as well as water or mixtures of water with one or more of the organic solvents mentioned.

Depending on the nature of the oxidizing agent used, the reaction according to the invention is generally carried out at a pH value of 3 to 12. Adjustment of the pH value can be achieved by adding an appropriate acid or base. Acids or bases which may be used here are those which do not decompose the starting compounds or the end products and do not cause a decrease in the activity of the oxidizing agents. Rather, it is desirable that they increase the activity of the oxidizing agents. Examples of inorganic acids which can be used are hydrochloric acid or sulphuric acid, and examples of organic acids which can be used are acetic acid or formic acid. Examples of appropriate bases are ammonium hydroxide, alkali metal hydroxides, alkaline earth metal hydroxides, alkali metal carbonates, alkaline earth metal carbonates, alkali metal alcoholates and alkali metal salts and alkaline earth metal salts of carboxylic acids.

The pH value can be adjusted before the start of the reaction and/or during the reaction.

The reaction according to the invention is generally carried out at a temperature of from −20° to 100° C., preferably from 0° to 70° C. The reaction time is generally from half an hour to 50 hours. In general, the reaction is carried out under normal pressure.

The protective groups which may still be present in the molecule after the reaction may be split off in a known manner by alkaline or acid hydrolysis, selective hydrogenolysis or displacement reactions. If a compound which contains an acyl protective group(s) of the type (1) and/or (2) is used in the cleaving reaction, this can preferably be split off using an aqueous solution of an alkali metal hydroxide or alkaline earth metal hydroxide.

If, for example, 1, 2′, 3, 6′-tetra-N-ethoxycarbonyl-sicomycin and sodium periodate are used as starting materials, the course of the reaction can be represented by the following equation:

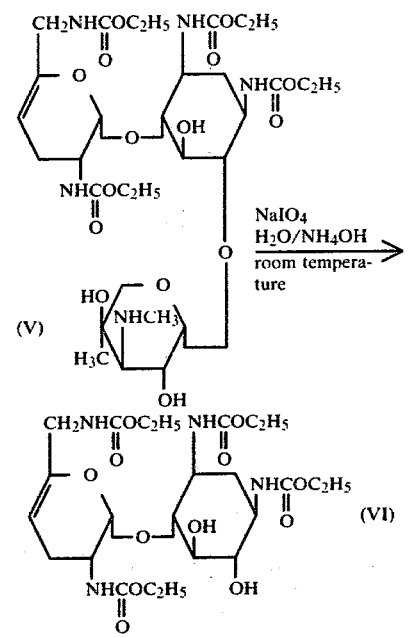

The starting compound of formula (V) which can be used according to the invention is accessible by the process described in German patent application No. P2726197.8 corresponding to our co-pending European Patent Application No. 78100099.7 by reacting sisomycin with diethyl pyrocarbonate in aqueous alcohol. In principle, the oxidative cleaving of (V) can be carried out using any one of the above mentioned oxidizing agents; however, the use of sodium periodate, which is employed in the form of an aqueous solution, is preferred in the present case. Suitable solvents for the cleaving reaction in the present case are, preferably, methanol or a methanol/water mixture. The reaction is advantageously carried out with the addition of from 5 to 10% concentrated ammonium hydroxide. The preferred reaction temperature is from −5° to +5° C. Further processing is conveniently carried out by evaporating the reaction mixture in vacuo, extracting the residue with ethanol and deionising the extracts with a basic ion exchanger resin (OH$^\ominus$form).

The reaction product thus obtained can be used directly or, if desired, can be purified by chromatography or fed to the "Barry degradation", that is to say the reaction with N,N-dimethylhydrazine in acetic acid [compare P.S.O'Colla in Methods in Carbohydrate Chemistry 5, 382–392 (1965)].

After working up, the tetra-N-ethoxycarbonyl compound of the formula (VI) is obtained in high yield as a crystalline product. Splitting off the protective groups in an aqueous alkaline solution gives the free disaccharide of the formula (VII)

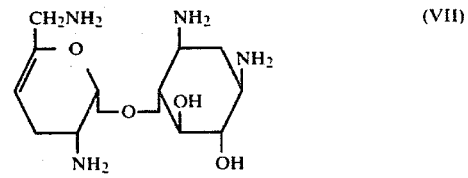

which was hitherto unknown.

The compounds according to the invention are antimicrobial agents having a broad spectrum of action and a particular activity against Gram-negative bacteria. These properties make it possible to use them as medicaments in combating bacterial diseases in warm-blooded animals. They are suitable, in medicine, for the prophylaxis and chemotherapy of local and systemic infections caused by Gram-negative bacteria, for example E. coli, Proteus, Klebsiella and Pseudomonas.

In addition, the disaccharides according to the invention are extremely valuable intermediate products for the synthesis of pseudo-trisaccharides, which can be used as valuable antibiotics.

Thus, by using the intermediate products according to the invention, a new and advantageous route is opened for the preparation of the known antibiotics 66-40 B and 66-40 D, which were hitherto only formed, to the extent of about 2% in each case, in the fermentative preparation of sisomycin (DT-OS (German Published Specification) No. 2,437,160).

In this procedure, the tetra-N-acyldisaccharide which is formed in the oxidative cleaving of, for example, tetra-N-acyl-sisomycins and which still has two free hydroxyl groups can be reacted, in the course of a glycosidation reaction by mathods which are known in carbohydrate chemistry, with a reactive mono-saccharide derivative, such as, for example, an appropriate protected glycosyl halide of 3-desoxy-3-methylamino-L-arabinopyranose, the glycosidic linking taking place at the hydroxyl group on C-6 as expected [S. Umezawa, Advan. Carbohydr. Chem. 30, 111 (1974)].

The subsequent deblocking of the glycosidation products by known methods gives the desired pseudo-trisaccharide.

If partially blocked aminotrisaccharides are used for the oxidation reaction, N-protected pseudo-disaccharides are obtained (see, for example, formula VI) which can be converted into semi-synthetic aminotrisaccharides by known glycosidation reactions.

EXAMPLE 1
4-O-(2,6-Diamino-2,3,4,6-tetradesoxy-α-D-glycerohex-4-enopyranosyl)-2-desoxystreptamine A solution of 2.88 g (13.4 mmols) of $NaIO_4$ in 40 ml of water is slowly added to 2 g (4.47 mmols) of sisomycin in 20 ml of water at 0° C., whilst stirring. After 2 hours, the mixture is evaporated to dryness under a high vacuum. The residue is stirred with ethanol and after 15 minutes the mixture is filtered.

The filtrate is concentrated to a syrup, which is taken up in 40 ml of water, 2.4 ml = 1.9 g (32 mmols) of N,N-dimethylhydrazine is added, the pH is adjusted to 6 with acetic acid and the mixture is stored overnight at 40° C. The brown-yellow solution is diluted and discharged on to an acid ion exchanger ®Amberlite IRC 50 (Trade Mark), H+ form. Using 2 N ammonia, the product is eluted from the ion exchanger, which has been thoroughly washed until neutral. The eluate is evaporated to dryness under a high vacuum. An amorphous, colourless solid is obtained.

EXAMPLE 2
4-O-(2,6-Di-benzyloxycarbonylamino-2,3,4,6-tetradesoxy-α-D-glycero-hex-4-enopyranosyl)-1,3-di-N-benzyloxycarbonyl-2-desoxystreptamine The product obtained according to Example 1 is stirred overnight in 7 ml of methanol/water 5:2 with 0.85 ml of carbobenzoxy chloride and 0.3 g of $Na_2CO_3$. The mixture is diluted with water until all the salts have dissolved and is filtered. The residue is washed with water, methanol and petroleum ether, stirred in as little $CHCl_3$ as possible and filtered off again. The white residue is washed with a little $CHCl_3$ and reprecipitated from pyridine using methanol.

Melting point = 244°–246.5° C. $[\alpha]_D^{28} = +61.5°$ (c = 1.0, pyridine).

Analysis for $C_{44}H_{48}N_4O_{12}$: calculated: C 64.06; H 5.87; N 6.79. Found: C 63.69; H 5.88; N 6.79.

EXAMPLE 3
4-O-(2,6-Di-ethoxycarbonylamino-2,3,4,6-tetradesoxy-α-D-glycero-hex-4-enopyranosyl)-1,3-di-N-ethoxycarbonyl-2-desoxystreptamine 0.83 g (3.9 mmols) of $NaIO_4$ in 10 ml of water are slowly added dropwise to a solution of 950 mg (1.3 mmols) of tatra-N-ethoxycarbonyl-sisomycin in 15 ml of methanol and 1 ml of concentrated ammonium hydroxide at 0° C., whilst stirring. After removing the cooling means, the mixture is stirred at room temperature for one hour and then evaporated to dryness under a high vacuum. The residue is stirred in 30 ml of methanol, 30 ml of ethanol are added and the mixture is stirred for 15 minutes and filtered. The residue is washed with ethanol. The filtrate is treated with a strongly basic ion exchanger (Amberlite (Trade Mark) IRA 400) and concentrated to a syrup. The syrup is taken up in 40 ml of methanol, 0.89 ml = 0.7 g (11.6 mmols) of N,N-dimethylhydrazine are added, the pH is adjusted to 6.5 with acetic acid and the mixture is stored overnight at 40° C. The brown-yellow coloured solution is diluted with water, neutralised with $Na_2CO_3$ and evaporated to dryness under a high vacuum. The residue is stirred with $CHCl_3$ and extracted by shaking with water. The aqueous phase is separated off. The organic phase is dried over $MgSO_4$ and concentrated. The residue is taken up in a little methanol, the mixture is diluted with ether and, after adding petroleum ether, is stored in a deep-freeze. 370 mg, and in a second precipitation 150 mg, of tetra-N-carboethoxy-sisomycin in the form of a pale yellow power was obtained. Yield 530 mg (71%). For characterisation, the powder is reprecipitated from methanol/ether using petroleum ether.

$[\alpha]_{-D}^{23} + 107°$ (c = 1.0, $CH_3OH$) Melting point 213.5°–215.0° C.

Analysis for $C_{24}H_{44}N_4O_{15}$: calculated C 49.65, H 7.64; N 9.65; found C 49.68; H 7.03; N 9.60.

EXAMPLE 4
4-O-(2,6-Di-acetamido-2,3,4,6-tetradesoxy-α-D-glycero-hex-4-enopyranosyl)-1,3-di-N-acetyl-2-desoxystreptamine 1.9 g of 1,2′,3,6′-tetra-N-acetylsisomycin in 20 ml of water are added dropwise to a solution of 3 g of potassium hexacyanoferrate-III and 900 mg of potassium hydroxide in 20 ml of water at 60° C. A solution of 9 g of potassium hexacyano-ferrate-III and 1 g of potassium hydroxide in 90 ml of water is then added dropwise to this solution in the course of 1.5 hours. After the addition has ended, 250 ml of acetone are added, the inorganic material which has precipitated is filtered off and the filtrate is freed from the solvent in vacuo. The residue thus obtained is extracted with 10 ml of a mixture consisting of equal parts of methylene chloride and methanol, the extracts are filtered and the filtrate is evaporated in vacuo. 1.1 g of the title compound, which is crystallised from ethanol/ether for purification, are thus obtained.

$[\alpha]_D^{23} = +170°$ (c=1.0, CH$_3$OH) Melting point 238.5°–242.0° C.

Analysis for C$_{20}$H$_{32}$N$_4$O$_8$: calculated: C. 52.61; H. 7.06; N. 12.27; Found: C. 51.92; H. 7.19; N. 11.87.

EXAMPLE 5

4-O-(2,6-Diamino-2,3,4,6-tetradesoxy-α-D-glycero-hex-4-enopyranosyl)-2-desocystreptamine from 4-O-(2,6-di-acetamido-2,3,4,6-tetradesoxy-α-D-glycero-hex-4-enopyranoxyl)-1,3-di-N-acetyl-2-desoxystreptamine 410 mg of 4-O-(2,6-di-acetamido-2,3,4,6-tetradesoxy-α-D-glycero-hex-4-enopyranosyl)-1,3-di-N-acetyl-2-desoxystreptamine and 5 g of Ba(OH)$_2$×8H$_2$O are heated in 5 ml of water for 6 hours at an oil bath temperature of 110°–120° C., whilst stirring. The mixture is then diluted with water, neutralised by adding solid carbon dioxide and filtered through a fritted glass filter. The residue is washed with water. The filtrate is concentrated to about 40 ml, adjusted to pH 6 with 2 N H$_2$SO$_4$ and filtered and the filtrate is evaporated to dryness. The residue is taken up in a little methanol/water, filtered off and dried. Yield 421 mg (97%) of amorphous solid as the sulphate.

What is claimed is:

1. A process for the preparation of a compound, an acid-addition salt or an N-protected derivative thereof, said compound having the formula

    (I)

in which

Y is a radical of the formula

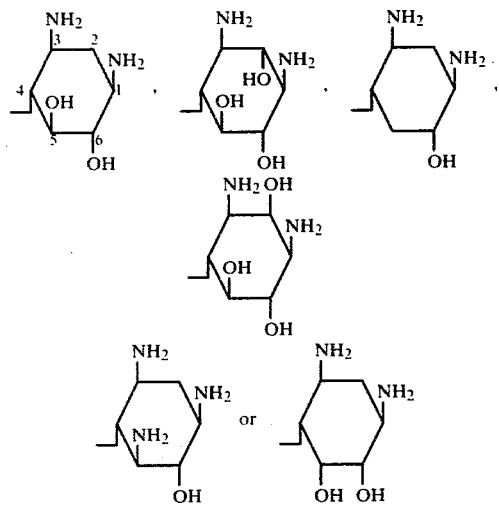

and X is a radical of the formula

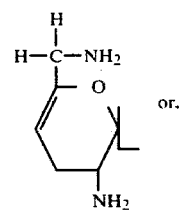

when Y is a radical of the formula

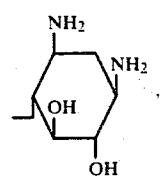

X is a radical of the formula

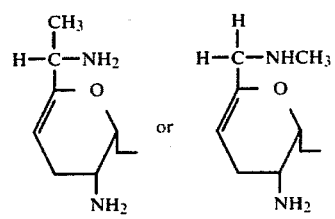

the bond between X and Y being a (1→4)-glycosidic bond in each case, which comprises cleaving a compound of the formula

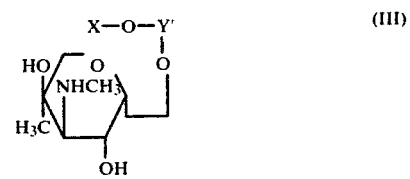    (III)

in which

Y' is a radical

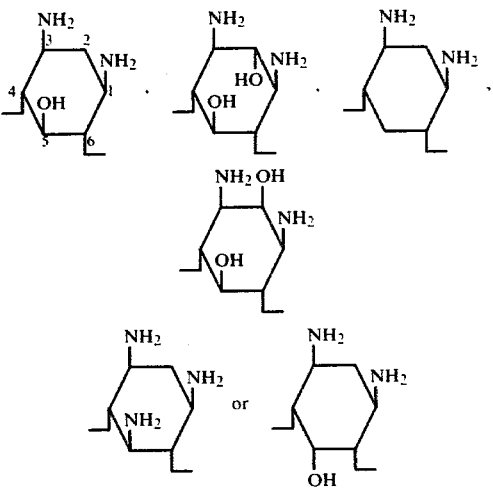

which is linked glycosidically with the radical X in the 4-position and glycosidically with the garosaminyl radical attached to said radical Y' in the 6-position and in which X is a radical of the formula

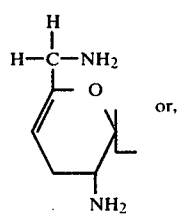

when Y' is a radical of the formula

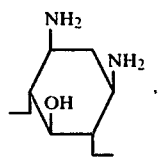

X is a radical of the formula

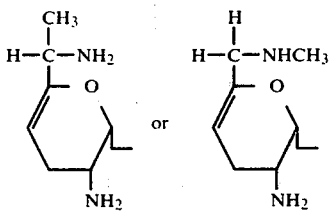

in free form or in the form of an N-protected derivative, by treatment with an oxidizing agent selected from the groups consisting of manganese dioxide, sodium periodate, potassium hexacyanoferrate-III and potassium permanganate so as to product groups which are present and isolating the compound of the formula (I).

2. A process according to claim 1 in which the reaction is carried out at from −20° to +100° C.

3. A process according to claim 1 in which the reaction is carried out in the presence of an inert solvent.

* * * * *